(12) United States Patent
Bruna et al.

(10) Patent No.: US 11,478,192 B2
(45) Date of Patent: Oct. 25, 2022

(54) APPARATUS FOR SENSING COMPRISING A FLEXIBLE SUBSTRATE

(71) Applicant: Nokia Technologies Oy, Espoo (FI)

(72) Inventors: Matteo Bruna, Cambridge (GB); Ugo Sassi, Cambridge (GB); Salvatore Zarra, Bordentown, NJ (US); Zoran Radivojevic, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 231 days.

(21) Appl. No.: 16/763,132

(22) PCT Filed: Nov. 16, 2018

(86) PCT No.: PCT/FI2018/050839
§ 371 (c)(1),
(2) Date: May 11, 2020

(87) PCT Pub. No.: WO2019/106229
PCT Pub. Date: Jun. 6, 2019

(65) Prior Publication Data
US 2020/0390393 A1 Dec. 17, 2020

(30) Foreign Application Priority Data
Nov. 29, 2017 (EP) .................................... 17204376

(51) Int. Cl.
  *G01B 7/00* (2006.01)
  *A61B 5/00* (2006.01)
  (Continued)

(52) U.S. Cl.
  CPC ............ *A61B 5/6804* (2013.01); *A41D 1/005* (2013.01); *G01B 7/16* (2013.01); *H05K 1/189* (2013.01);
  (Continued)

(58) Field of Classification Search
  CPC .......... A61B 5/6804; A61B 2562/0261; A61B 2562/164; A41D 1/005; G01B 7/16; H05K 1/189; H05K 2201/10151
  See application file for complete search history.

(56) References Cited

U.S. PATENT DOCUMENTS

| 7,665,288 B2 | 2/2010 | Karayianni et al. |
| 8,945,328 B2 * | 2/2015 | Longinotti-Buitoni ..................... A61B 5/6805 156/247 |

(Continued)

FOREIGN PATENT DOCUMENTS

| CN | 103764222 A | 4/2014 |
| CN | 104188739 A | 12/2014 |

(Continued)

OTHER PUBLICATIONS

Gu et al., "Soft Capacitor Fibers Using Conductive Polymers for Electronic Textiles", Smart Materials and Structures, vol. 19, No. 11, Jun. 26, 2010, pp. 1-13.

(Continued)

*Primary Examiner* — Max H Noori
(74) *Attorney, Agent, or Firm* — Harrington & Smith

(57) ABSTRACT

An apparatus includes a flexible substrate; at least one sensor mounted on the flexible substrate arranged to provide an electrical output signal dependent upon a first parameter; and at least one conductive trace provided on the flexible substrate arranged to provide a direct current path to the at least one sensor and having an electrical property dependent upon a second parameter and arranged to provide an electrical output signal indicative of the second parameter.

18 Claims, 3 Drawing Sheets

(51) Int. Cl.
*A41D 1/00* (2018.01)
*G01B 7/16* (2006.01)
*H05K 1/18* (2006.01)

(52) U.S. Cl.
CPC . *A61B 2562/0261* (2013.01); *A61B 2562/164* (2013.01); *H05K 2201/10151* (2013.01)

(56) References Cited

U.S. PATENT DOCUMENTS

| | | | |
|---|---|---|---|
| 8,948,839 B1* | 2/2015 | Longinotti-Buitoni | A61B 5/7405 600/382 |
| 10,325,472 B1* | 6/2019 | Harsdorff | A61B 5/1117 |
| 2005/0054941 A1* | 3/2005 | Ting | A61B 5/296 600/534 |
| 2014/0070957 A1* | 3/2014 | Longinotti-Buitoni | A61B 5/02055 340/870.01 |
| 2014/0318699 A1* | 10/2014 | Longinotti-Buitoni | A61B 5/743 156/247 |
| 2015/0164427 A1 | 6/2015 | Volpe et al. | |
| 2015/0199045 A1 | 7/2015 | Robucci et al. | |
| 2016/0000374 A1 | 1/2016 | Dandekar et al. | |
| 2016/0186366 A1 | 6/2016 | McMaster | |
| 2016/0270700 A1 | 9/2016 | Baxi et al. | |
| 2016/0301482 A1* | 10/2016 | Konanur | H04B 13/005 |
| 2017/0082418 A1 | 3/2017 | Gong | |
| 2017/0196513 A1* | 7/2017 | Longinotti-Buitoni | A61B 5/7278 |
| 2017/0248033 A1 | 8/2017 | Moniz et al. | |
| 2019/0094088 A1* | 3/2019 | Reif | A61B 5/6807 |
| 2019/0307404 A1* | 10/2019 | Wiebe | A61B 5/7221 |
| 2020/0253294 A1* | 8/2020 | Van De Zande | G06F 3/016 |
| 2020/0375537 A1* | 12/2020 | Carlile | A61B 5/27 |
| 2022/0013955 A1* | 1/2022 | Shen | H01R 13/2421 |
| 2022/0026284 A1* | 1/2022 | Clements | G01K 7/22 |

FOREIGN PATENT DOCUMENTS

| | | |
|---|---|---|
| CN | 106996796 A | 8/2017 |
| WO | 2015/101759 A1 | 7/2015 |
| WO | 2017/013493 A1 | 1/2017 |
| WO | 2017/075703 A1 | 5/2017 |
| WO | 2017/080984 A1 | 5/2017 |

OTHER PUBLICATIONS

Stoppa et al., "Wearable Electronics and Smart Textiles: A Critical Review—MDPI", Sensors, vol. 14, 2014, pp. 11957-11992.
"How to Measure Joint Angle with Stretch Sensors", StetchSense, Retrieved on Apr. 29, 2020, Webpage available at : https://stretchsense.com/article-resources/case-study/how-to-measure-joint-angle-with-stretch-sensors/.
Extended European Search Report received for corresponding European Patent Application No. 17204376.2, dated May 28, 2018, 8 pages.
International Search Report and Written Opinion received for corresponding Patent Cooperation Treaty Application No. PCT/FI2018/050839, dated Feb. 26, 2019, 13 pages.
Office action received for corresponding Chinese Patent Application No. 201880077083.0, dated Jun. 24, 2021, 8 pages of office action and 4 pages of translation available.

* cited by examiner

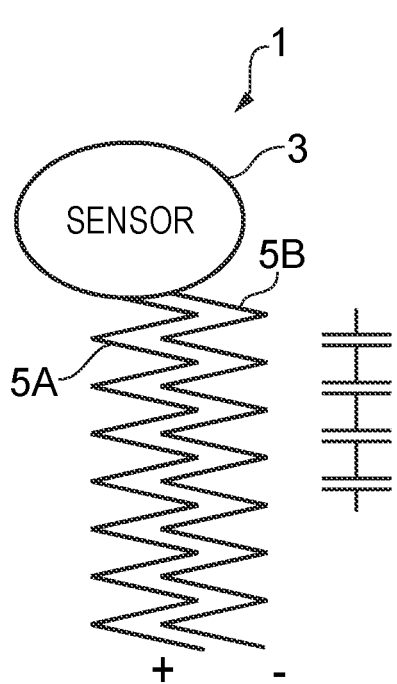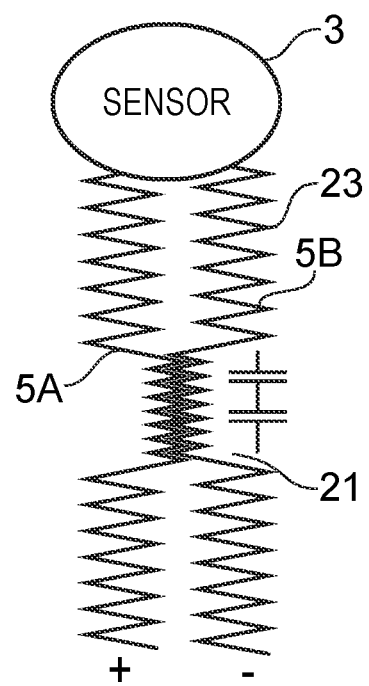
FIG. 2A FIG. 2B
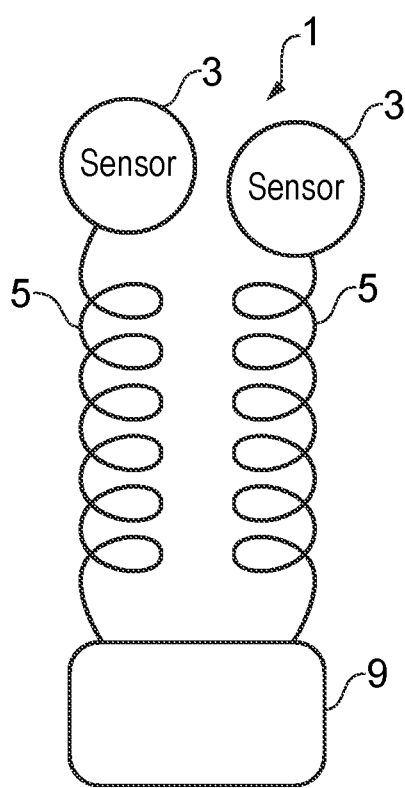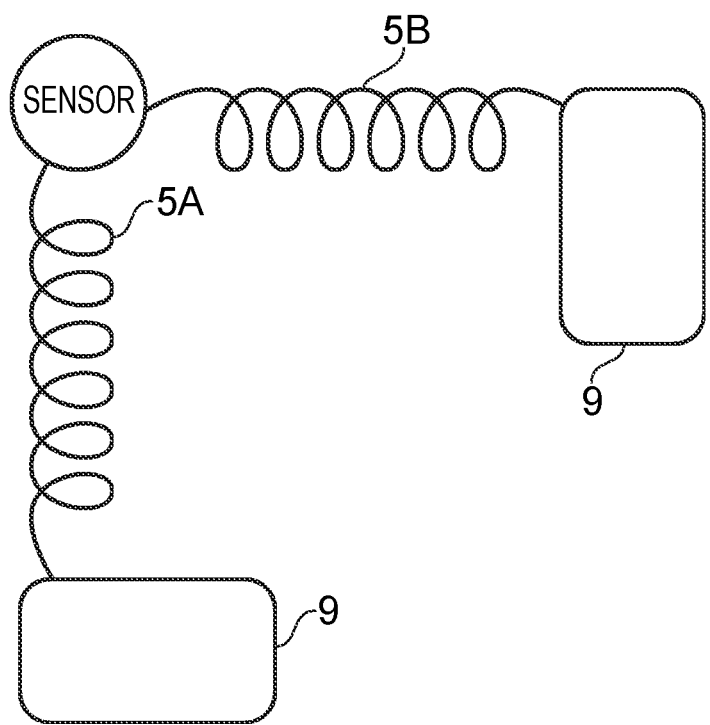
FIG. 3 FIG. 4

APPARATUS FOR SENSING COMPRISING A FLEXIBLE SUBSTRATE

RELATED APPLICATION

This application claims priority to PCT Application No. PCT/FI2018/050839, filed on Nov. 16, 2018, which claims priority to European Application No. 17204376.2, filed on Nov. 29, 2017, each of which is incorporated herein by reference in its entirety.

TECHNOLOGICAL FIELD

Examples of the disclosure relate to apparatus for sensing.

BACKGROUND

Apparatus for sensing are known. It can be useful to integrate such sensors into wearable garments so that they can be used to monitor the physical condition of a subject wearing the garment.

BRIEF SUMMARY

According to various, but not necessarily all, examples of the disclosure there is provided, an apparatus comprising: a flexible substrate; at least one sensor mounted on the flexible substrate arranged to provide an electrical output signal dependent upon a first parameter; and at least one conductive trace provided on the flexible substrate arranged to provide a direct current path to the at least one sensor and have an electrical property dependent upon a second parameter and arranged to provide an electrical output signal indicative of the second parameter.

The conductive trace may be deformable and the second parameter may be the deformation of the conductive trace. The output signal indicative of the second parameter may be used to create a database of deformation of the conductive trace.

The conductive trace may be arranged to provide power to the at least one sensor.

The conductive trace may be arranged to provide a signal line to the at least one sensor.

The electrical property of the conductive trace dependent upon a second parameter may comprise at least one of: capacitance, impedance, resistance.

The apparatus may be arranged to provide a direct current signal to the at least one sensor to measure the first parameter and to provide an alternating current signal to the conductive trace to measure the second parameter.

The apparatus may comprise a first conductive trace and a second conductive trace wherein at least a portion of the first conductive trace is positioned adjacent to the second conductive trace so as to provide capacitance between the first conductive trace and the second conductive trace.

The apparatus may comprise a first conductive trace and a second conductive trace wherein at least a portion of the first conductive trace extends towards a direction perpendicular to the second conductive trace so as to enable deformation of the conductive traces to be monitored in two dimensions.

At least part of the conductive trace may be arranged in a zig-zag arrangement.

At least part of the conductive trace may be arranged in a coiled arrangement.

The flexible substrate may be part of a garment which can be worn by a subject.

The first parameter detected by the at least one sensor may comprise a biometric parameter of a subject.

The at least one sensor may be arranged to detect haptic feedback from the subject.

The conductive traces may comprise a dielectric coating.

The apparatus may comprise controlling circuitry.

According to various, but not necessarily all, examples of the disclosure, there are provided examples as claimed in the appended claims.

BRIEF DESCRIPTION

For a better understanding of various examples that are useful for understanding the detailed description, reference will now be made by way of example only to the accompanying drawings in which:

FIGS. 2A and 2B illustrate example apparatus;

FIG. 3 illustrates an example apparatus;

FIG. 4 illustrates another example apparatus;

Figure 6:
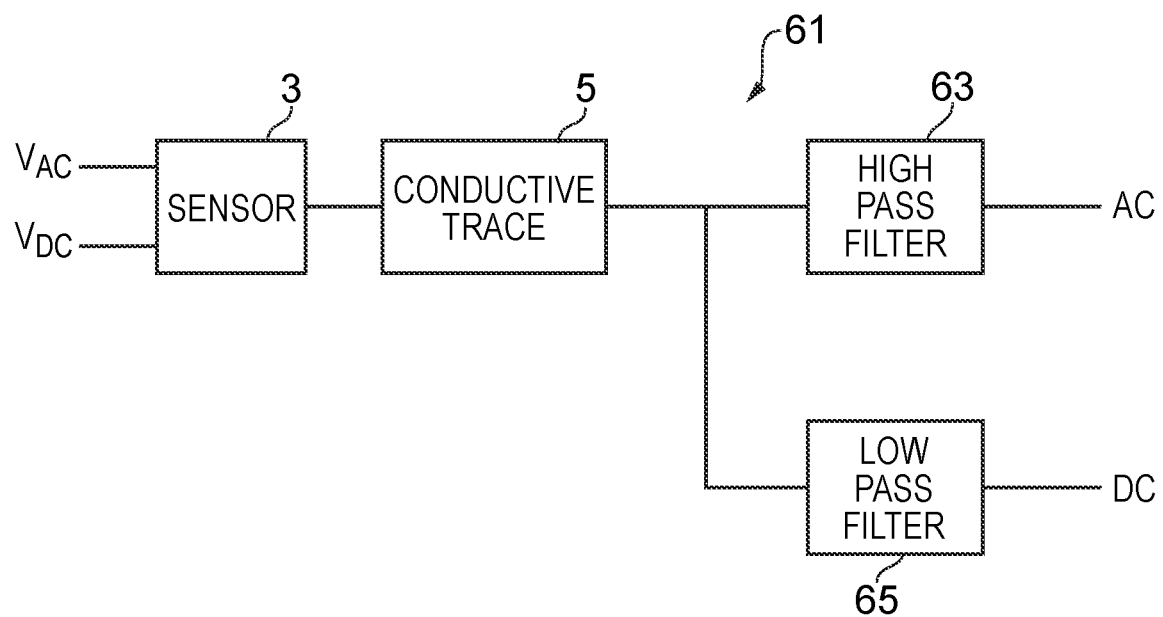

FIG. 6 schematically illustrates example circuitry which may be used with example apparatus.

DETAILED DESCRIPTION

Examples of the disclosure relate to a sensing apparatus 1. The apparatus 1 may be integrated within a wearable garment and, in some examples, may be used to detect biometric parameters, haptic feedback or other suitable parameters relating to a subject wearing the garment. The apparatus 1 comprises one or more sensors 3 arranged to detect a first parameter of a subject. The apparatus 1 also comprises conductive traces 5 which are arranged to provide a direct current path to the sensors 3. The direct current path may be used to provide power and/or signals to the sensors 3. The conductive traces 5 are also arranged so that one or more electrical properties of the conductive traces are dependent upon a second parameter. This enables the conductive traces 5 to perform a plurality of functions, namely providing power and/or signals to the sensor 3 and also sensing the second parameter.

Figure 1:
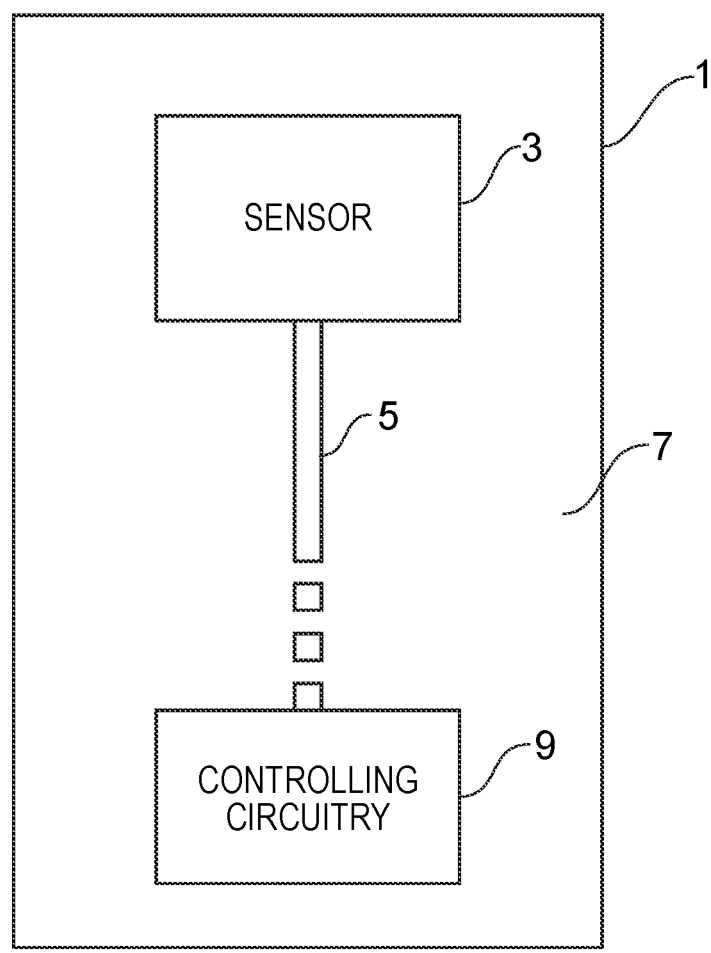
FIG. 1 illustrates an example apparatus.

FIG. 1 schematically illustrates an example apparatus 1 according to examples of the disclosure. The apparatus 1 comprises a sensor 3, a conductive trace 5 and a flexible substrate 7. In the example of FIG. 1 controlling circuitry 9 is also shown.

The flexible substrate 7 provides support for one or more sensors 3. In some examples one or more sensors 3 may be mounted upon a surface of the substrate 7. In some examples the one or more sensors 3 may be integrated within the substrate 7 so that the sensors 3 are embedded, or at least partially embedded within the substrate 7.

The flexible substrate 7 comprises any suitable material. In some examples the flexible substrate 7 may comprise textile or fabric which may be suitable for use in a wearable garment. The flexible substrate 7 may be formed from a material that can be easily deformed by the subject. For instance it may be formed from a material that will bend and/or stretch when a force is applied by a subject.

The flexible substrate 7 may form part of a garment which can be worn by a subject. In some examples the flexible substrate 7 may form part of a glove or shirt or other garment which can be worn by a subject. In some examples the flexible substrate 7 may form part of a cuff or any other suitable item that can attached to a body of a subject.

Where the flexible substrate 7 forms part of a wearable garment the one or more sensors 3 may be positioned on the substrate 7 so that when a subject wears the garment the one or more sensors 3 are positioned adjacent, or in close proximity to, the skin of the subject. This may enable biometric parameters of the subject or haptic feedback from the subject to be detected by the one or more sensors 3. In some examples the one or more sensors 3 may be provided so that they are in direct contact with the skin of the subject. In other cases an insulating layer may be provided between the one or more sensors 3 and the skin of the subject.

It is to be appreciated that the one or more sensors 3 may also be used to measure parameters other than biometric parameters of the subject. For example the one or more sensors 3 could be arranged to detect environmental parameters such as temperature, humidity and/or the presence of analytes. In some examples the one or more sensors 3 could be used for determining the location of the subject. For example the one or more sensors 3 could comprise GPS (global positioning system) sensors, Bluetooth sensors or any other type of sensors that may be used for positioning. In such examples the one or more sensors 3 may be positioned on any suitable location on the substrate 7 which need not be adjacent to the subject's skin.

The one or more sensors 3 may comprise any means which may be arranged to detect a first parameter. The sensors 3 may be arranged to provide an electrical output signal dependent upon the first parameter.

In some examples the first parameter may comprise a biometric parameter of a subject. The biometric parameter may comprise any time varying signal that is generated by the subject's body. The biometric parameter may comprise an autonomic parameter. The autonomic parameter may be controlled subconsciously by the subject. The biometric parameter could comprises temperature, humidity, blood oxygen levels, hear rate, audio signals, pressure, presence of one or more analytes or any other suitable parameters.

In some examples the biometric parameter may comprise a bioelectrical signal. The bioelectrical signals comprise electrical signals that are generated within the subject's body. The bioelectrical signals could be generated by the subject's heartbeat, by electrical activity of the subject's brain or other parts of their nervous system or by any other part of the subject's body. In some examples the bioelectric signal could comprise at least one of an electrocardiogram signal, electroencephalogram signal, electromyogram signal, electrooculogram signal, electrogastrogram signal, galvanic skin potential or any other suitable bioelectrical signal.

In some examples the biometric parameter may comprise a biomechanical signal. The biomechanical signal could be controlled consciously or subconsciously by the user. In some examples the biomechanical signals may comprise mechanical signals that are generated within the subject's body by the subject's heartbeat, respiration, abdominal sounds or other body movements. In some examples the biomechanical signal could comprise at least one of ballistocardiogram signal, seismocardiogram signal, phonocardiogram signal or any other suitable signal.

In some examples one or more sensors 3 may be arranged to detect haptic feedback from the subject. In such examples the one or more sensors 3 may comprise an actuator or any other suitable means. The one or more sensors 3 for detecting haptic feedback may be arranged to detect a change in pressure or capacitance, or any other suitable parameter, caused by movement of the subject. The haptic feedback could comprise conscious movement of the subject such as movement of their limbs or torso while performing an activity. The haptic feedback could comprise the subconscious movement of the subject such as the movement of the subject's torso due to breathing or their posture while they are sitting.

In some examples one or more sensors 3 may be arranged to detect parameters other than biometric parameters or haptic feedback from the subject. For example one or more sensors 3 may be able to detect ambient parameters such as temperature, sound or any other parameters indicative of the environment in which the subject is located.

In the example of FIG. 1 only one sensor 3 is shown. It is to be appreciated that in some examples the apparatus 1 may comprise a plurality of sensors 3. In some examples each of the sensors 3 may be arranged to detect the same parameter. In other examples the sensors 3 may be such that different sensors 3 may be arranged to detect different parameters. This may enable more information about the physical condition of the subject to be obtained.

The structure of the sensors 3 depends upon the parameter that is to be detected by the sensor 3. For example, where the sensors 3 are arranged to detect the temperature the sensor 3 may comprise a pyroelectric material or other means that produces a change in electrical signal when the temperature is changed. In examples where the sensors 3 are arranged to detect a pulse, the sensors 3 may comprise light sensors that can detect light reflected by the subject's skin or an electrical sensor arranged to detect the electrical signals generated by the pulse or any other suitable types of sensors 3. In examples where the sensors 3 are arranged to detect haptic feedback the one or more sensors 3 could comprise one or more capacitive electrodes arranged to detect a change in capacitance when the subject moves or changes their posture.

In the example apparatus 1 of FIG. 1 the sensor 3 is electrically connected to a conductive trace 5. The sensor 3 is electrically connected to the conductive trace 5 so as to provide a direct current path between the conductive trace 5 and the sensor 3. The direct current path comprises a galvanic connection between the conductive trace 5 and the sensor 3. It is to be appreciated that both alternating current signals and direct current signals can be transmitted via the direct current path.

The conductive trace 5 has an electrical property which is dependent upon a second parameter. The second parameter may be different to the first parameter that is detected by the sensor 3. The electrical property of the conductive trace 5 changes as the second parameter is changed so as to provide an electrical output signal indicative of the second parameter.

The conductive trace 5 is also provided on the flexible substrate 7. In some examples the conductive trace 5 may be provided on a surface of the flexible substrate 7. In some examples the conductive trace 5 may be embedded within, or at least partially embedded within, the flexible substrate 7. For instance where the flexible substrate 7 comprises a textile or fabric the conductive trace 5 could be embedded within the weave of the textile or fabric. In some examples the conductive trace 5 may comprise a structural component of a garment. For instance, the conductive trace 5 could be a thread or other means to couple two or more parts of the garment together. In such cases the conductive trace 5 may be located, at least in part, within the seams of the garment.

In some examples of the disclosure the conductive trace 5 is a deformable conductive trace 5. In such examples the conductive trace 5 may bend and/or stretch and/or otherwise deform when the flexible substrate 7 is deformed. In such examples the second parameter that controls the electrical property of the conductive trace 5 may be the deformation of the conductive trace 5.

The electrical property of the conductive trace 5 that is responsive to the second parameter may comprise any suitable electrical property. For instance, the electrical property may comprise at least one of; capacitance, impedance, resistance.

The conductive trace 5 may comprise any suitable conductive material. For example the conductive trace 5 may comprise copper, silver, carbon or any other suitable electrically conductive material. In some examples the conductive trace 5 may comprise a non-conductive material, such as yarn or thread, which can then be covered in a conductive material. In some examples the conductive trace 5 may be covered, or at least partially covered with a dielectric coating. The dielectric coating may comprise any suitable material and may be arranged on the surface of the conductive trace 5 so as to enhance the electrical properties of the conductive trace 5. In some examples the dielectric coating may comprise a polymer with a high dielectric constant such as a silicone or polyurethane based material.

The conductive trace 5 may be arranged to provide a signal line to the sensor 3. In such examples the conductive trace 5 may be coupled to controlling circuitry 9 and may be arranged to provide signals between the controlling circuitry 9 and the sensor 3. The conductive trace 5 may be arranged so that the electrical output signal indicative of the first parameter is provided from the sensor 3 to the controlling circuitry 9 via the conductive trace 5.

The conductive trace 5 may be arranged to provide power to the sensor 3. In such examples the conductive trace 5 may be coupled to a power sources and may be arranged to provide power from the power source to the sensor 3.

In some examples the same conductive trace 5 may be arranged to provide power to the sensor 3 and also to provide a signal line. In such examples only a single conductive trace 5 might be provided to the sensor 3. In some examples a plurality of conductive traces 5 may be coupled to any one sensor 3. This may enable different conductive traces 5 to perform different functions. For instance, a first conductive trace 5 may be arranged as a signal line and a second conductive trace 5 may be arranged to provide power to the sensor 3.

In examples of the disclosure the conductive trace 5 may be coupled to controlling circuitry 9 as shown in FIG. 1. The conductive trace 5 may be directly or indirectly coupled to the controlling circuitry 9. One or more intervening components may be provided between the conductive trace 5 and the controlling circuitry 9. In the example of FIG. 1 the controlling circuitry 9 is provided on the same flexible substrate 7 as the sensor 3 and the conductive trace 5. In other examples the controlling circuitry 9 could be provided on a different flexible substrate 7. In some examples the controlling circuitry 9 could be provided as part of a different apparatus 1. In such examples the conductive trace 5 may be coupled to a transmitter which may enable information to be transmitted to the controlling circuitry 9.

The controlling circuitry 9 may comprise means for controlling the apparatus 1. The controlling circuitry 9 may comprise processing circuitry and memory circuitry. The controlling circuitry 9 may comprise means for providing a control signal to the sensor 3. The controlling circuitry 9 may comprise means for obtaining an electrical output signal from the conductive trace 5 and separating the obtained electrical output signal into a component corresponding to the first parameter detected by the sensor and a component corresponding to the second parameter detected by the conductive trace 5.

In some examples the controlling circuitry 9 may be arranged to provide a direct current signal to the sensor 3. The direct current signal is provided via the conductive trace 5 and is used to enable the sensor 3 to measure the first parameter. The controlling circuitry 9 may also be arranged to provide an alternating current signal to the conductive trace 5. The alternating current signal may be used to measure the change in the electrical property of the conductive trace 5 and so provides a measurement of the second parameter. The alternating current signal may have a frequency that is high enough so that it does not interfere with the operation of the sensor 3. In some examples the alternating current signal may have a frequency of 1 MHz or above. The alternating current signal may also have a lower power compared to the direct current signal so that the alternating current signal does not interfere with the operation of the sensor 3.

FIGS. 2A and 2B illustrate example apparatus 1 according to implementations of the disclosure.

In the examples of FIGS. 2A and 2B the apparatus 1 comprises a sensor 3, a first conductive trace 5A and a second conductive trace 5B. The sensors 3 and the conductive traces 5A, 5B may be as described above. The apparatus 1 may also comprise a flexible substrate 7 and controlling circuitry 9 which may be as described above. The example apparatus 1 may be provided within a wearable garment which may be worn by a subject.

In the example of FIGS. 2A and 2B both the first conductive trace 5A and the second conductive trace 5B are coupled to the sensor 3 to provide a direct current path to the sensor 3. The first conductive trace 5A provides a positive conductive trace and the second conductive trace 5B provides a negative conductive trace.

In the examples of FIGS. 5A and 5B the electrical property of the conductive traces 5A, 5B that is dependent upon the second parameter is the capacitance. In these examples at least a portion of the first conductive trace 5A is positioned adjacent to the second conductive trace 5B so as to provide capacitance between the first conductive trace 5A and the second conductive trace 5B. In the examples of FIGS. 5A and 5B at least a portion of the first conductive trace 5A is positioned adjacent to the second conductive trace 5B. In other examples the portions of the conductive traces 5A, 5B could be substantially parallel or positioned at a different angle.

In some examples the first conductive trace 5A and the second conductive trace 5B may be positioned close to each other so that the electric field generated by the conductive traces 5A, 5B is confined to the gap between the conductive traces 5A, 5B. This may reduce the effect of any interference caused by the body of the subject. In some examples the conductive traces 5A, 5B may be covered, or at least partially covered, in a dielectric coating so as to increase the capacitance between the conductive traces 5A, 5B.

In some examples the conductive traces 5A, 5B may be arranged in an alternating arrangement. The alternating arrangement may comprise a plurality of switch-back turns.

The switch-back turns comprise a turn or bend which has an angle greater than 90 degrees so that adjacent portions the conductive trace 5A, 5B extends towards opposing directions. For example a first portion extends substantially towards the rights and then a second portion, following a switch-back turn extends substantially towards the left.

In the examples of FIGS. 2A and 2B both of the conductive traces 5A, 5B are arranged in a zig-zag arrangement. In other examples just part of the conductive traces 5A, 5B could be arranged in the zig-zag arrangement. The zig-zag arrangement comprises adjacent sections of the conductive traces 5A, 5B extending towards opposing, or substantially opposing, directions. In the zig-zag arrangement the switch-back turns provide sharp corners. In other examples the switch-back turns could be curved or any other suitable shape.

In some examples of the disclosure the alternating arrangement may enable the conductive traces 5A, 5B to be deformed. For example the alternating arrangement may enable the conductive traces to be stretched and/or compressed.

In the example of FIG. 2A the conductive traces 5A, 5B are arranged so that there is a uniform, or substantially uniform, distance between the first conductive trace 5A and the second conductive trace 5B along the length of the traces 5A, 5B. When the apparatus 1 is deformed, for example when the subject moves or changes their posture, this may cause stretching of the conductive traces 5A, 5B. The stretching decreases the distance between the conductive traces 5A, 5B and so increases the capacitance between the conductive traces 5A, 5B. The increase in capacitance can be measured using an alternating current signal. This enables the amount of stretching of the conductive traces 5A, 5B to be determined from the change in the capacitance.

In the example of FIG. 2A the conductive traces 5A, 5B enable any change in capacitance along the length of the conductive traces 5A, 5B to be determined.

In the example of FIG. 2B the conductive traces 5A, 5B are arranged so that the conductive traces 5A, 5B have a first portion 21 in which the conductive traces 5A, 5B are positioned closer together and a second portion 23 in which the conductive traces 5A, 5B are positioned further away from each other. In the second portion 23 the conductive traces 5A, 5B may be positioned further away from each other so that there is negligible capacitance between the two conductive traces 5A, 5B in this portion 23.

When the apparatus 1 of FIG. 2B is stretched this causes the distance between the two conductive traces 5A, 5B to be decreased and so changes the capacitance between the two conductive traces 5A, 5B. The capacitance in the first portion 21 is larger than the capacitance in the second portion 23 so that the measured change in capacitance corresponds to the change in capacitance in the first portion 21. This enables the first portion 21 of the conductive traces 5A, 5B to provide a sensing portion. In this example this allows the change in capacitance at the sensing portion 21 to be measured but does not measure the change in capacitance outside of the sensing portion. This may enable a deformation of the conductive traces 5A, 5B in a particular location to be identified.

In examples where the conductive traces 5A, 5B are provided within a wearable garment the first portion 21 of the conductive traces 5A, 5B may be arranged to be positioned in a location of the garment which is likely to undergo a lot of movement and deformation. For instance if the garment is a glove the first portion 21 may be positioned so that it is located over a joint of a finger or thumb. If the garment is a shirt then the first portion 21 may be arranged so that it is positioned in the elbow joint, or shoulder portion or any other suitable position within the shirt.

FIG. 3 illustrates an example apparatus 1 in which at least part of the conductive trace 5 is arranged in a coiled arrangement. The apparatus 1 illustrated in FIG. 3 comprises two sensors 3, two conductive traces 5 and controlling circuitry 9. The sensors conductive traces 5 and controlling circuitry 9 may be as described above in relation to FIG. 1.

In the example of FIG. 3 two sensors 3 are provided. In some examples the sensors 3 may be arranged to detect different parameters. In other examples the sensors 3 may be arranged to detect the same parameter but at different locations within the apparatus 1. In the example of FIG. 3 the sensors 3 are illustrated as being adjacent to each other. It is to be appreciated that they could be provided in any suitable arrangement and need not be provided adjacent to each other.

In the example of FIG. 3 both of the traces got to the same controlling circuitry 9. This enables the same controlling circuitry 9 to be used to process signals obtained by a plurality of sensors 3 and a plurality of conductive traces 5. In other examples more than one controlling circuitry 9 may be used.

In the example of FIG. 3 the electrical property of the conductive traces 5 that is dependent upon the second parameter is the inductance. In the example of FIG. 3 the conductive traces are provided in a coiled arrangement. As the conductive traces 5 are stretched and/or compressed this changes the number of coils per unit length for the conductive traces 5 and so enables an output signal indicative of the stretching or compression of the conductive trace 5 to be provided.

In the example apparatus 1 of FIG. 3 the two conductive traces 5 are positioned adjacent to each other and extending parallel or at least substantially parallel to each other. In order to reduce the mutual inductance between the two coils the conductive traces 5 may be covered, or at least partially covered, in a dielectric coating.

FIG. 4 illustrates another example apparatus 1. In the example of FIG. 4 two conductive traces 5A, 5B are provided to the same sensor 3. In some examples the two conductive traces 5A, 5B may provide different functions for the sensor 3. For instance, the first conductive trace 5A may be provided as a signal line and the second conductive trace 5B may be arranged to provide power to the sensor 3. Other functions for the conductive traces 5A, 5B could be used in other examples of the disclosure.

In the example of FIG. 4 both of the conductive traces 5A, 5B extend between the sensor 3 and some controlling circuitry 9. In some examples the conductive traces 5A, 5B and the controlling circuitry 9 may be arranged so that both of the conductive traces 5A, 5B are coupled to the same controlling circuitry 9. In other examples different controlling circuitry 9 may be provided and different conductive traces 5A, 5B may be coupled to the different controlling circuitry 9.

In the example apparatus 1 of FIG. 4 at least a portion of the first conductive trace 5A extends towards a direction perpendicular to the second conductive trace 5B so as to enable deformation of the conductive traces 5A, 5B to be monitored in two dimensions. In the example of FIG. 4 the coiled portions of the two conductive traces 5A, 5B are provided in a perpendicular arrangement. In other examples the coiled portions could be provided in a different angular arrangement. In such examples the coiled portions of the conductive traces 5A, 5B could still be used to obtain information about the deformation of the conductive traces 5A, 5B in two dimensions. In such examples algorithms, or any other suitable process, could be used to adjust for the conductive traces 5A, 5B not being perpendicular to each other.

Figure 5:
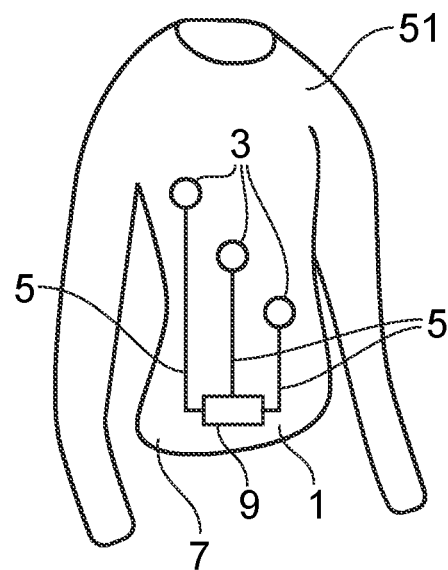
FIG. 5 illustrates a garment comprising an example apparatus.

Having the conductive traces 5A, 5B in a perpendicular arrangement also reduces the mutual inductance between the two coils FIG. 5 illustrates a garment 51 comprising an example apparatus 1. The garment 51 comprises an item of clothing which is arranged to be worn by a subject. The subject could be a person or an animal which may generate biometric parameters. In the example of FIG. 5 the garment 51 comprises a shirt. Other items of clothing could be used in other examples of the disclosure.

In the example of FIG. 5 the apparatus 1 comprises a plurality of sensors 3. In the example of FIG. 5 three sensors 3 are shown. Other numbers of sensors 3 could be used in other examples of the disclosure.

The sensors 3 are positioned within the garment 51 so as to enable the sensors 3 to detect biometric parameters from the subject. The position of the sensors 3 within the garment 51 may be dependent upon the parameter that the sensors 3 are intended to detect. In the example of FIG. 5 the sensors 3 are positioned on a front panel of the shirt so that the sensors 3 may be located adjacent to the subject's chest or torso when the shirt is worn by the subject.

Each of the sensors 3 is coupled to a conductive trace 5 which provides a direct current path between controlling circuitry 9 and the sensors 3. The conductive traces 5 could be provided in any suitable arrangement as described above.

In examples where the conductive traces 5 are arranged to have a sensing first portion 21 and a non-sensing second portion 23, the sensing first portion may be positioned within the garment 51 so that the sensing first portion 21 is located in an area which is likely to undergo deformation. For example it may be located around the subject's shoulder or elbow.

In the example of FIG. 5 the controlling circuitry 9 is provided within the garment 51. In other examples the garment 51 may comprise a transmitter which enables the output signals from the sensors 3 and the conductive traces 5 to be transmitted to another controlling circuitry 9 in another device. The other device could be a mobile computing device or any other suitable type of device. In some examples the garment 51 could comprise memory circuitry which may enable the output signals from the sensors 3 and the conductive traces 5 to be stored so that they can be transferred to controlling circuitry 9 and/or permanent storage at a later point.

In some examples the controlling circuitry 9 may be arranged to use the output signal indicative of the second parameter obtained from the conductive traces 5 to create a database of deformation of the conductive trace 5. This database may provide a profile of movement of the subject. Information obtained from the other sensors 3 may also be stored as part of the profile. As the apparatus is provided within a garment 51 which could be worn for a long period of time, for example several hours, this enables the movement of the subject to be monitored over that time period. As the conductive traces 5 may be located in any part of the garment 51 may enable a large amount of information about the movement of the subject to be obtained.

FIG. 6 schematically illustrates example circuitry 61 which may be used with example apparatus.

The input signal that is provided to the sensor 3 comprises both a direct current component and an alternating current component. The direct current component may enable the parameter sensed by the sensor 3 to be measured while the alternating current component may enable the parameter sensed by the conductive trace 5 to be measured. The direct current component may have a higher power level than the alternating current component. The alternating current component may have a high frequency so as not to interfere with the measurements made by the sensor 3. In some examples the input signal may be provided to the sensor via the conductive trace 5.

The output signal provided by the conductive trace 5 comprises a direct current signal that comprises information indicative of the first parameter and an alternating current signal that comprises information indicative of the second parameter. In the example of FIG. 6 the signals are provided to a high pass filter 63 to enable the alternating current component to be determined and to a low pass filter 65 to enable the direct current component to be determined. Other means for separating the respective signals may be used in other examples of the disclosure.

Example of the disclosure provide the technical effect that the conductive traces 5 can provide multiple functions. The conductive traces 5 can detect parameters such as deformation, this may reduce the number of sensors 3 that are required within a garment 51 or apparatus as separate deformation sensors 3 might not be needed. The conductive traces 5 provide power and/or a signal to the sensors 3 which may reduce the total number of components within the garment 51 or apparatus 1.

In some examples the conductive trace 5 may also act as a thread or as part of the weave within the flexible substrate 7. This may enable the conductive trace 5 to provide a structural component within a garment 51. This may enable the conductive trace 5 to detect deformation of a user wearing the garment but may also make the garment simpler as the threads and other structural components form part of the electronic components.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
a flexible substrate;
at least one sensor mounted on the flexible substrate arranged to provide an electrical output signal dependent upon a first parameter; and
at least one conductive trace provided on the flexible substrate arranged to provide a direct current path to the at least one sensor and have an electrical property dependent upon a second parameter, and arranged to provide an electrical output signal indicative of the second parameter;
wherein the apparatus is arranged to provide a direct current signal to the at least one sensor to measure the first parameter and to provide an alternating current signal to the conductive trace to measure the second parameter.

2. An apparatus as claimed in claim 1 wherein the conductive trace is deformable and the second parameter is the deformation of the conductive trace.

3. An apparatus as claimed in claim 2 wherein the output signal indicative of the second parameter is used to create a database of deformation of the conductive trace.

4. An apparatus as claimed in claim 1 wherein the conductive trace is arranged to provide at least one of, power to the at least one sensor, a signal line to the at least one sensor.

5. An apparatus as claimed in claim 1 wherein the electrical property of the conductive trace dependent upon a second parameter comprises at least one of: capacitance, impedance, resistance.

6. An apparatus as claimed in claim 1 comprising a first conductive trace and a second conductive trace wherein at least a portion of the first conductive trace is positioned adjacent to the second conductive trace so as to provide capacitance between the first conductive trace and the second conductive trace.

7. An apparatus as claimed in claim 1 comprising a first conductive trace and a second conductive trace wherein at least a portion of the first conductive trace extends towards a direction perpendicular to the second conductive trace so as to enable deformation of the conductive traces to be monitored in two dimensions.

8. An apparatus as claimed in claim 1 wherein at least part of the conductive trace is arranged in an alternating arrangement.

9. An apparatus as claimed in claim 1 wherein at least part of the conductive trace is arranged in a coiled arrangement.

10. An apparatus as claimed in claim 1 wherein the flexible substrate is part of a garment which can be worn by a subject.

11. An apparatus as claimed in claim 1 wherein the first parameter detected by the at least one sensor comprises a biometric parameter of a subject.

12. An apparatus as claimed in claim 1 wherein the at least one sensor is arranged to detect haptic feedback from the subject.

13. An apparatus as claimed in claim 1 wherein the conductive traces comprise a dielectric coating.

14. An apparatus as claimed in claim 1 wherein the apparatus comprises controlling circuitry.

15. A method comprising:
mounting and arranging at least one sensor on a flexible substrate to provide an electrical output signal depending upon a first parameter;
providing at least one conductive trace on the flexible substrate;
arranging the at least one conductive trace to provide a direct current path to the at least one sensor; and
arranging the at least one conductive trace to provide an electrical output signal indicative of a second parameter;
wherein the method further comprises providing a direct current signal to the at least one sensor; measuring the first parameter; and providing an alternating current signal to the at least one conductive trace to measure the second parameter.

16. A method as claimed in claim 15 wherein the method further comprises deforming the conductive trace and measuring the deforming with the second parameter.

17. A method as claimed in claim 16 wherein the method further comprises creating a database of the deforming of the conductive trace.

18. A method as claimed in claim 15 wherein the method further comprises arranging the at least on conductive trace to provide power to the at least one sensor.

* * * * *